(12) United States Patent
Tai et al.

(10) Patent No.: US 11,345,675 B2
(45) Date of Patent: May 31, 2022

(54) COMPOUND, ANTI-ALLERGY DRUG, AND MEDIATOR RELEASE INHIBITOR

(71) Applicant: LAIMU CORPORATION, Yokohama (JP)

(72) Inventors: Akihiro Tai, Shobara (JP); Kaori Miura, Yokohama (JP); Sachio Wakayama, Yokohama (JP)

(73) Assignee: LAIMU CORPORATION, Kanagawa (JP)

( * ) Notice: Subject to any disclaimer, the term of this patent is extended or adjusted under 35 U.S.C. 154(b) by 0 days.

(21) Appl. No.: 17/057,344

(22) PCT Filed: Nov. 30, 2018

(86) PCT No.: PCT/JP2018/044160
§ 371 (c)(1),
(2) Date: Nov. 20, 2020

(87) PCT Pub. No.: WO2019/225035
PCT Pub. Date: Nov. 28, 2019

(65) Prior Publication Data
US 2021/0214328 A1 Jul. 15, 2021

(30) Foreign Application Priority Data

May 23, 2018 (JP) .............................. JP2018-098570

(51) Int. Cl.
*C07D 307/62* (2006.01)
*A61P 37/08* (2006.01)

(52) U.S. Cl.
CPC ............ *C07D 307/62* (2013.01); *A61P 37/08* (2018.01)

(58) Field of Classification Search
None
See application file for complete search history.

(56) References Cited

FOREIGN PATENT DOCUMENTS

| | | | | | |
|---|---|---|---|---|---|
| GB | 1016834 | * | 1/1966 | ........... | A61K 31/375 |
| JP | S61-263969 A | | 11/1986 | | |
| JP | 2000-351905 A | | 12/2000 | | |
| JP | 2015-003894 A | | 1/2015 | | |
| JP | 2017-031083 A | | 2/2017 | | |
| JP | 2019-006692 A | | 1/2019 | | |
| WO | 2009/014343 A2 | | 1/2009 | | |
| WO | 2014/050894 A1 | | 4/2014 | | |

OTHER PUBLICATIONS

Database Registry Chemical Abstracts Service, Columbus, Ohio, Accession No. RN 2206678-40-0, Entered STN: Apr. 5, 2018.*
International Preliminary Report on Patentability for corresponding Japanese PCT International Application No. PCT/JP2018/044160, dated Nov. 24, 2020, with English translation.
International Search Report and Written Opinion for corresponding PCT International Application No. PCT/JP2018/044160.
Tai, Akihiro et al., Vitamins., 2017, vol. 91, No. 9, pp. 579-580.
Kato, K. et al., Studies on Scavengers of Active Oxygen Species, 1. Synthesis and Biological Activity of 2-)-Alkylascorbic Acids, J. Med. Chem., 1988, vol. 31, pp. 793-798.
Iwaoka, Y. et al., Affinity resins as new tools for identifying target proteins of ascorbic acid, Analyst, Jan. 9, 2018, vol. 143, No. 4, pp. 874-882.
Japanese office action dated Jan. 5, 2022 in corresponding Japanese application No. 2018-098570.
Office Action dated Apr. 26, 2022 issued in the corresponding Japanese patent application No. 2018-098570 with its English Translation.

* cited by examiner

*Primary Examiner* — Samantha L Shterengarts
(74) *Attorney, Agent, or Firm* — Browdy and Neimark, PLLC

(57) ABSTRACT

A compound represented by the following formula has a high anti-allergy activity. $R^1$ represents a substituted or unsubstituted acyloxy group, or a substituted or unsubstituted acylamino group, $R^2$ represents a substituted or unsubstituted alkyl group.

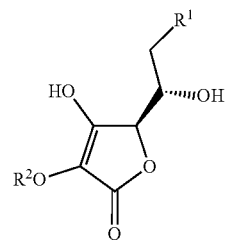

5 Claims, 1 Drawing Sheet

COMPOUND, ANTI-ALLERGY DRUG, AND MEDIATOR RELEASE INHIBITOR

TECHNICAL FIELD

The present invention relates to a compound useful as an anti-allergy agent and a mediator release inhibitor.

BACKGROUND ART

Recently, type I allergy sufferers such as pollen allergy sufferers are increasing. Type I allergy develops through release of a mediator such as histamine owing to degranulatory response of mast cells.

As a medical agent to suppress such an allergy symptom, an antihistamine having a histamine H1-receptor antagonistic activity has heretofore been much used. However, a histamine H1-receptor is known to exhibit, for example, a stimulant effect by histamine bonding thereto, and when an antihistamine that inhibits the bonding is taken, it may cause, for example, sleepiness, a sense of fatigue and dry throat side effects, and therefore care should be exercised in taking it.

Given the situation, PTL 1 proposes use of an acylated derivative of L-ascorbic acid as an active ingredient for an anti-allergy agent, and for example, in Examples therein, confirms that an acylated derivative of L-ascorbic acid with a glycosyl group introduced into the 2-position thereof, as represented by the following formula, exhibits an anti-allergy effect and a mediator release inhibiting effect. This literature says that the acylated derivative of L-ascorbic acid with a glycosyl group introduced into the 2-position thereof suppresses allergy symptoms owing to such a mediator release inhibiting effect, and therefore can evade side effects of sleepiness and others to be caused by a histamine H1-receptor antagonist.

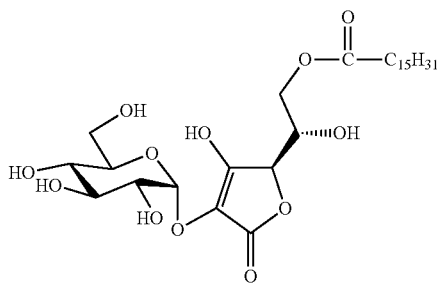

CITATION LIST

Patent Literature

PTL 1: JP-A-2017-31083

SUMMARY OF INVENTION

Technical Problem

As described above, an acylated derivative of L-ascorbic acid with a glycosyl group introduced into the 2-position thereof is known to have an anti-allergy action. However, the present inventors synthesized various derivatives of ascorbic acid and compared the anti-allergy activity therebetween, and have found that an acylated derivative of ascorbic acid with no glycosyl group introduced thereinto not shown in PTL 1 can exhibit a higher anti-allergy activity than the acylated derivative of ascorbic acid with a glycosyl group introduced thereinto.

Accordingly, the present inventors have made further studies about the anti-allergy activity of ascorbic acid derivatives, and have investigated further more for the purpose of finding out an ascorbic acid derivative having a higher anti-allergy activity.

Solution to Problem

As a result of assiduous studies made for the purpose of solving the above-mentioned problems, the present inventors have found that an ascorbic acid derivative, in which the 6-positioned hydroxy group is changed to an acyloxy group or an acylamino group and the 2-positioned hydroxy group is changed to an alkoxy group by introducing an alkyl group thereinto, has a higher anti-allergy activity and a higher mediator release inhibiting effect than an acylated derivative of ascorbic acid with a glycosyl group introduced into the 2-position thereof. The present invention has been made on the basis of such findings, and specifically has the following constitution.

[1] A compound represented by the following formula (1):

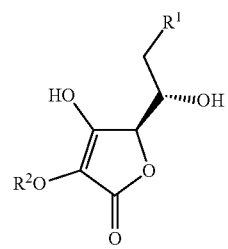

Formula (1)

In the formula (1), $R^1$ represents a substituted or unsubstituted acyloxy group, or a substituted or unsubstituted acylamino group, $R^2$ represents a substituted or unsubstituted alkyl group.

[2] The compound according to [1], wherein the carbon number of the acyloxy group and the acylamino group of $R^1$ in the formula (1) each is 10 or more.

[3] The compound according to [1] or [2], wherein $R^1$ in the formula (1) is a substituted or unsubstituted acylamino group.

[4] The compound according to [1] or [2], wherein $R^1$ in the formula (1) is an unsubstituted acyloxy group or an unsubstituted acylamino group.

[5] The compound according to any one of [1] to [4], wherein the carbon number of the alkyl group of $R^2$ in the formula (1) is 1 to 6.

[6] The compound according to any one of [1] to [5], wherein $R^2$ in the formula (1) is an unsubstituted alkyl group.

[7] An anti-allergy agent containing a compound represented by the formula (1) or an isomer thereof, or a pharmaceutically-acceptable salt thereof as an active ingredient.

[8] A mediator release inhibitor containing a compound represented by the formula (1) or an isomer thereof, or a pharmaceutically-acceptable salt thereof as an active ingredient.

Advantageous Effects of Invention

The compound of the present invention has a high anti-allergy activity and a high mediator release inhibiting effect, and is useful as an anti-allergy agent and a mediator release inhibitor. By using the compound of the present invention, an isomer thereof or a pharmaceutically-acceptable salt thereof as an active ingredient in an anti-allergy agent and a mediator release inhibitor, release of an inflammatory mediator accompanied by antigen-antibody reaction, as well as various allergy symptoms to occur after inflammatory mediator release can be effectively inhibited.

DESCRIPTION OF EMBODIMENTS

Figure 1:
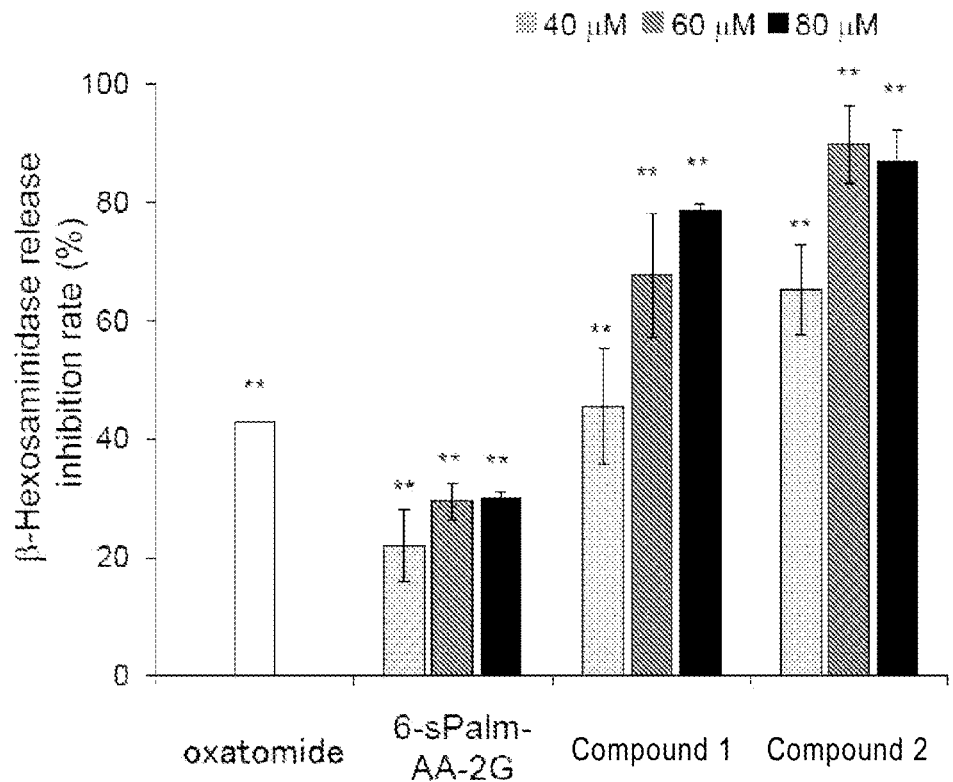
FIG. 1 This is a graph showing a β-hexosaminidase release inhibition rate of compound 1, compound 2, 6-sPalm-AA-2G and oxatomide.

In the following, the present invention is described in detail. The constitutional elements may be described below with reference to representative embodiments and specific examples of the invention, but the invention is not limited to the embodiments and the examples. In the description herein, a numerical range expressed as "to" means a range that includes the upper limit and/or the lower limit thereof.

Compound Represented by the Formula (1)

The compound of the present invention is a compound represented by the following formula (1).

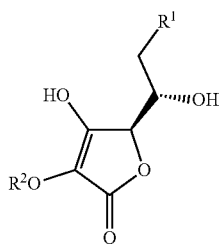

Formula (1)

In the formula (1), $R^1$ represents a substituted or unsubstituted acyloxy group, or a substituted or unsubstituted acylamino group. Preferably, the carbon number of the acyloxy group and the acylamino group of $R^1$ is 10 or more, more preferably 12 or more. The compound represented by the formula (1) where the carbon number of the acyloxy group and the acylamino group of $R^1$ is larger tends to have a higher anti-allergy activity and a higher mediator release inhibiting effect. The upper limit of the carbon number of the acyloxy group and the acylamino group is not specifically limited, and can be appropriately defined in consideration of, for example, the physical properties of the compound and the vehicle to be used in pharmaceutical formulation. For example, a compound where the carbon number of the acyloxy group or the acylamino group of $R^1$ is 16 or less has a relatively high solubility in water, and can be therefore dissolved in an aqueous vehicle or the like. On the other hand, for example, a compound where the carbon number of the acyloxy group or the acylamino group is 18 or more has a high lipophilicity, for which, therefore, an oily vehicle or an emulsifiable vehicle can be used. Of the acyloxy group and the acylamino group, the acylamino group is preferred since the compound having the group can have an increased anti-allergy activity and an increased mediator release inhibiting effect Preferably, the substituted or unsubstituted acyloxy group of $R^1$ has a structure represented by the following formula (2).

Formula (2)

In the formula (2), $R^{11}$ represents a substituted or unsubstituted alkyl group, and * indicates a bonding position to the 6-position in the formula (1).

The alkyl group of $R^{11}$ may be any of linear, branched or cyclic, but is preferably linear. When the alkyl group is linear, the compound represented by the formula (1) can exhibit a higher anti-allergy activity and a higher mediator release inhibiting effect. For the same reason as that described for the acyloxy group hereinabove, the carbon number of the alkyl group is preferably 9 or more, more preferably 11 or more, even more preferably 13 or more. The upper limit of the carbon number of the alkyl group is not specifically limited, but is, from the viewpoint of easy availability of raw materials and easiness in introduction into the 6-position, preferably 23 or less. Examples of the alkyl group include a nonyl group ($C_9H_{19}$), an undecyl group ($C_{11}H_{23}$), a tridecyl group ($C_{13}H_{27}$), and a pentadecyl group ($C_{15}H_{31}$). In terms of the acyl group (—$COR^{11}$) in the formula (2), examples thereof include a decanoyl group having 10 carbon atoms, a dodecanoyl group having 12 carbon atoms, a tetradecanoyl group having 14 carbon atoms, and a hexadecanoyl group (palmitoyl group) having 16 carbon atoms. Above all, a palmitoyl group is most preferred. The alkyl group of $R^{11}$ may be substituted with a substituent. The substituent capable of substituting on the alkyl group include a hydroxy group, a halogen atom, an aryl group having 6 to 40 carbon atoms, an alkenyl group having 2 to 10 carbon atoms, and an alkynyl group having 2 to 10 carbon atoms, for example. These substituents may be further substituted with a substituent. At least one methylene group existing in the substituted or unsubstituted alkyl group represented by $R^{11}$ may be replaced with an ether group (—O—) or a carbonyl group (—CO—). However, both neighboring methylene groups are not replaced with an ether group (—O—) or a carbonyl group (—CO—). In this description, an acyl group includes an aroyl group.

Preferably, the substituted or unsubstituted acylamino group of $R^1$ has a structure represented by the following formula (3).

Formula (3)

In the formula (3), $R^{21}$ represents a substituted or unsubstituted alkyl group, $R^{22}$ represents a hydrogen atom or a substituent. * indicates a bonding position to the 6-position in the formula (1).

Regarding the description and the preferred range and specific examples of the alkyl group of $R^{21}$, reference may be made to the description and the preferred range and specific examples of the alkyl group of $R^{11}$. The alkyl group of $R^{21}$ may be substituted with a substituent. Regarding the preferred range of the substituent, reference may be made to the preferred range of the substituent for the alkyl group of $R^{11}$ described hereinabove.

$R^{22}$ may be a hydrogen atom or a substituent. The substituent that $R^{22}$ may have includes an alkyl group having 1 to 10 carbon atoms, an aryl group having 6 to 40 carbon atoms, an alkenyl group having 2 to 10 carbon atoms, and an alkynyl group having 2 to 10 carbon atoms, for example. These substituents may be further substituted with a substituent. At least one methylene group existing in the substituent represented by $R^{22}$ may be replaced with an ether group (—O—) or a carbonyl group (—CO—). However, both neighboring methylene groups are not replaced with an ether group (—O—) or a carbonyl group (—CO—).

In the formula (1), $R^2$ represents a substituted or unsubstituted alkyl group. When $R^2$ is a substituted or unsubstituted alkyl group, that is, when the 2-positioned hydroxy group of ascorbic acid is alkylated, high reductiveness of the compound can be reduced and therefore the stability of the compound against light, heat, oxygen, metal ions and the like can be thereby enhanced. The alkyl group of $R^2$ may be any of linear, branched or cyclic, but is preferably linear. The carbon number of the group is preferably 1 to 20, more preferably 1 to 10, even more preferably 1 to 6, further more preferably 1 to 4. Examples of the group include a methyl group, an ethyl group, an n-propyl group and an isopropyl group. The substituent capable of substituting on the alkyl group include an aryl group having 6 to 40 carbon atoms, a heteroaryl group having 3 to 40 carbon atoms, an alkenyl group having 2 to 10 carbon atoms, and an alkynyl group having 2 to 10 carbon atoms and the like. These substituents may be further substituted with a substituent. At least one methylene group existing in the substituted or unsubstituted alkyl group represented by $R^2$ may be replaced with an ether group (—O—) or a carbonyl group (—CO—). However, both neighboring methylene groups are not replaced with an ether group (—O—) or a carbonyl group (—CO—).

In the following, specific examples of the compound represented by the formula (1) are exemplified. However, the compound represented by the formula (1) usable in the present invention should not be limitatively interpreted by these specific examples. In the following formulae, Me represents a methyl group.

Compound 1

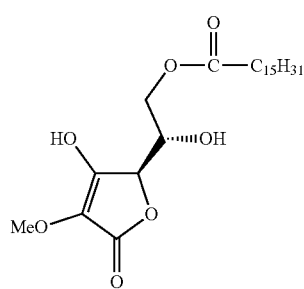

Compound 2

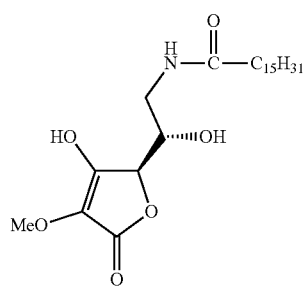

Synthesis Method for Compound Represented by Formula (1)

The compound represented by the formula (1) is a novel compound.

The compound represented by the formula (1) can be synthesized by combining known reactions. For example, a compound of the formula (1) where $R^1$ is a group represented by the formula (2) (acyloxy group) can be synthesized, starting from an acylated derivative of a commercially-available ascorbic acid, introducing a protective group X into the 3-positioned hydroxy group of the starting substance to give an intermediate 1a, then reacting the intermediate 1a with an alkyl halide to introduce an alkyl group into the 2-positioned hydroxy group, and thereafter deprotecting the protective group X from the resultant intermediate 2a using an acid such as hydrochloric acid or formic acid to give the intended compound.

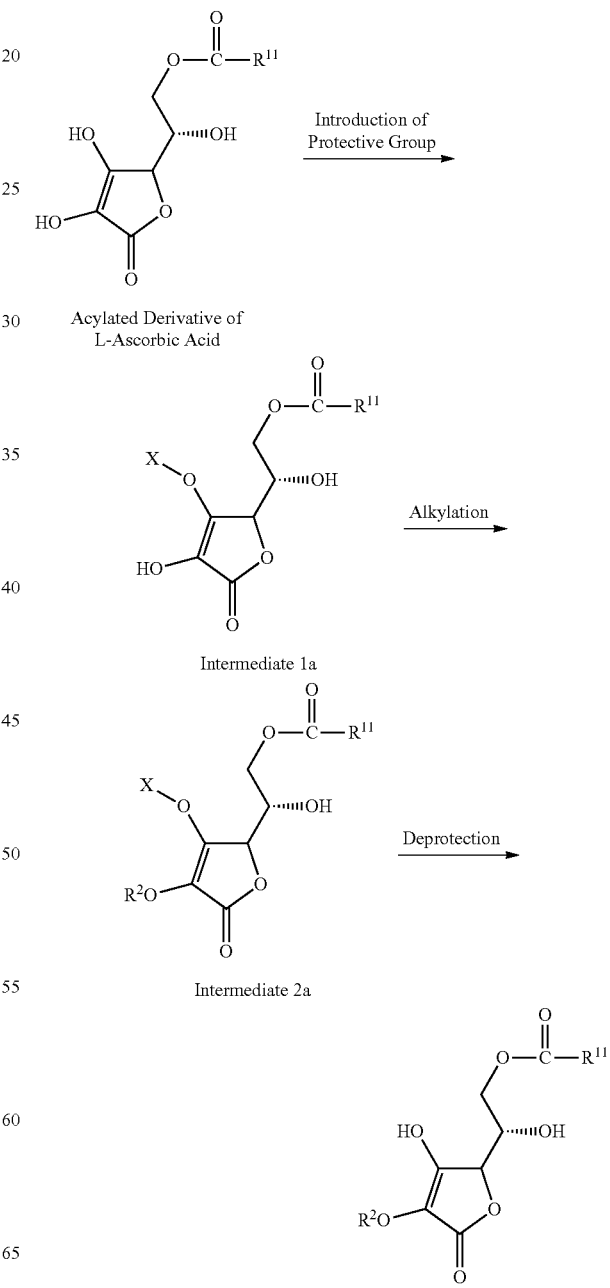

Regarding the description of $R^2$ in the above reaction formula, reference may be made to the description of $R^2$ in the formula (1), and regarding the description of $R^{11}$, reference may be made to the description of $R^{11}$ in the formula (2). X represents a protective group, such as a methoxymethyl group.

The starting substance in the above reaction formula, acylated derivative of L-ascorbic acid can be synthesized by acylating a commercial product, L-ascorbic acid. The acylating agent includes, for example, an acid, an acid halide, an acid anhydride or an acid ester. More specifically, the agent incudes, for example, a carboxylic acid such as decanoic acid, dodecanoic acid (lauric acid), myristic acid, and palmitic acid, and an acid halide, an acid anhydride, and a carboxylate.

A compound of the formula (1) where $R^1$ is a group represented by the formula (3) where $R^{22}$ is a hydrogen atom (acylamino group) can be synthesized, starting from a commercially-available ascorbic acid, introducing an alkyl group into the 2-position of the ascorbic acid according to the method described in Kato K. et al., J. Med. Chem., 31, 793-798 (1988) to give an intermediate 1b, then converting the 6-positioned hydroxy group in the intermediate 1b into an amino group to give an intermediate 2b, according to the method described in U.S. Pat. No. 4,368,330, and further introducing a saturated fatty acid into the 6-positioned amino group in the intermediate 2b to give the intended compound.

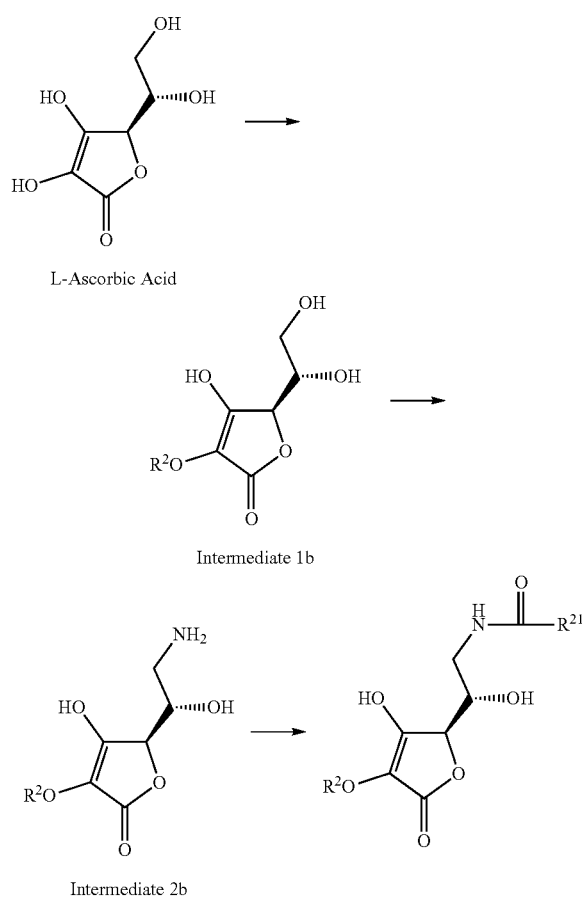

Regarding the description of $R^2$ in the above reaction formula, reference may be made to the description of $R^2$ in the formula (1), and regarding the description of $R^{21}$, reference may be made to the description of $R^{21}$ in the formula (3).

Regarding the details of these reactions, reference may be made to Synthesis Examples to be given hereinunder. The compound represented by the formula (1) may also be synthesized by combining any other known synthesis reactions.

Thus synthesized, the compound represented by the formula (1) can be purified according to a known method. Examples of the purification method include salting-out, dialysis, filtration, concentration, fractional precipitation, separatory extraction, gel chromatography, ion-exchange chromatography, high-performance liquid chromatography, gas chromatography, affinity chromatography, gel electrophoresis, isoelectric focusing electrophoresis, and crystallization. These methods may be combined for purification.

Usefulness of Compound Represented by Formula (1)

The compound of the present invention represented by the formula (1) has such a structure that the 6-positioned hydroxy group of L-ascorbic acid is substituted with an acyloxy group or an acylamino group and further the 2-positioned hydroxy group thereof is converted into an alkoxy group through introduction of an alkyl group thereinto, and therefore shows a higher anti-allergy activity and a higher mediator release inhibiting effect than an acylated derivative of L-ascorbic acid with a glycosyl group introduced into the 2-position thereof. In addition, the compound represented by the formula (1) expresses an anti-allergy effect through a mediator release inhibiting effect, and therefore can evade side effects such as sleepiness, a sense of fatigue and dry throat that are problematic in a histamine H1 receptor antagonist (antihistamine agent). Further, the compound represented by the formula (1) can be metabolized in a living body (human or mammal) to be an ascorbic acid, and is therefore extremely highly safe, and is, in addition, expected to exhibit an activity such as an antioxidant action of ascorbic acid. Accordingly, the compound represented by the formula (1) is highly useful as an active ingredient for an anti-allergy agent and a mediator release inhibitor.

Anti-Allergy Agent and Mediator Release Inhibitor

Next, the anti-allergy agent and the mediator release inhibitor of the present invention are described.

Anti-Allergy Agent

The anti-allergy agent of the present invention contains a compound represented by the formula (1) or an isomer thereof, or a pharmaceutically-acceptable salt thereof as an active ingredient. Here, "pharmaceutically-acceptable" means that the salt is free from any undesirable side effects such as nausea, dizziness and vomiting accompanied by administration thereof and from immune response to the pharmaceutical preparation in frequent administration thereof. In the following description, "a pharmaceutically-acceptable salt" may be simply referred to as "a salt".

Regarding the description of the compound represented by the formula (1) for use in the anti-allergy agent, reference may be made to the description in the section of "Compound represented by formula (1)" given hereinabove.

As described above, the compound represented by the formula (1) is a derivative of L-ascorbic acid in which the 6-positioned hydroxy group of L-ascorbic acid is converted into a substituted or unsubstituted acyloxy group or a substituted or unsubstituted acylamino group and the 2-positioned hydroxy group is converted into a substituted or unsubstituted alkoxy group. An isomer of the compound represented by the formula (1) includes derivatives of D-ascorbic acid, L-araboascorbic acid and D-araboascorbic acid (also referred to as erythorbic acid or isoascorbic acid) in which the 6-positioned hydroxy group is converted into a substituted or unsubstituted acyloxy group or a substituted or unsubstituted acylamino group and the 2-positioned hydroxy group is converted into a substituted or unsubstituted alkoxy group. In each derivative, regarding the description of the substituted or unsubstituted acyloxy group and the substituted or unsubstituted acylamino group at the 6-position, reference may be made to the description of $R^1$ in the formula (1), and regarding the description of the substituted or unsubstituted alkyl group that constitutes the 2-positioned substituted or unsubstituted alkoxy group, reference may be made to the description of $R^2$ in the formula (1). Of those derivatives, erythorbic acid derivatives are favorably used as easily available. It is known that ascorbic acid isomers have the same function as that of L-ascorbic acid (see, e.g., Suzuki et al., J. Nutr. Sci. Vitaminol., 41, 17-24, 1995), and derivatives of those isomers can also be used in the same manner as that for L-ascorbic acid derivatives that are the compounds represented by the formula (1).

Salts of the compound represented by the formula (1) and an isomer thereof may be salts with an inorganic ion, or salts with an organic ion, but are preferably poorly toxic ones. The inorganic ion capable of forming a salt with the compound represented by the formula (1) or an isomer thereof includes various cations of alkali metals (e.g., sodium, potassium), ammonium, alkaline earth metals (e.g., calcium, magnesium, strontium, barium), aluminum and the like. The organic ion capable of forming a salt with the compound represented by the formula (1) or an isomer thereof includes various cations derived from organic bases such as trimethylamine, triethylamine, pyridine, picoline, N,N-dibenzylethylenediamine, ethanolamine, diethanolamine, trishydroxymethylaminomethane, and dicyclohexylamine. Preferably, the compound represented by the formula (1) and an isomer thereof form salts with each cation of sodium, potassium, magnesium, calcium or aluminum, among the above.

Here, the compound represented by the formula (1) and an isomer thereof may form salts with any one alone of these cations, or may form a salt with two or more thereof. In the compound represented by the formula (1) and an isomer thereof, the site to be an anion moiety is not specifically limited, and for example, the proton of the 3-positioned hydroxy group may be dissociated to give an anion, or the proton of the substituent in $R^2$ may be dissociated to give an anion.

The anti-allergy agent of the present invention may contain one alone or two or more kinds of a compound represented by the formula (1) or an isomer thereof or a salt thereof. The compound represented by the formula (1) and an isomer thereof and a salt thereof that the anti-allergy agent contains all may be the same or may be composed of two or more kinds of them.

The anti-allergy agent of the present invention contains a compound represented by the formula (1) or an isomer thereof, or a salt thereof as an active ingredient, and therefore can effectively suppress allergy symptoms of living bodies and is especially effective against type I allergy. Specifically, the anti-allergy agent can suppress symptoms of rhinitis, conjunctivitis, bronchial asthma, food allergy, anaphylaxis, urticaria, or atopic dermatitis. The allergen of allergy to which the anti-allergy agent is applied is not specifically limited, and examples thereof include pollens, ticks, animal scurf, mold, chemical substances, and dietary proteins.

Mediator Release Inhibitor

The mediator release inhibitor of the present invention contains a compound represented by the formula (1) or an isomer thereof, or a pharmaceutically-acceptable salt thereof as an active ingredient. Regarding the description, the preferred range and specific examples of these active ingredients, reference may be made to the corresponding description in the section of (Anti-allergy agent) given hereinabove.

The mediator release inhibitor of the present invention contains a compound represented by the formula (1) or an isomer thereof, or a pharmaceutically-acceptable salt thereof as an active ingredient, and therefore can prevent release of an inflammatory mediator such as histamine to cause type I allergy. Type I allergy develops through release of an inflammatory mediator such as histamine owing to degranulatory response of mast cells. The active ingredient that the mediator release inhibitor of the present invention contains can suppress degranulatory response of mast cells to exhibit a mediator release inhibiting effect, and accordingly can suppress development of type I allergy.

Form of Anti-Allergy Agent and Mediator Release Inhibitor

The anti-allergy agent and the mediator release inhibitor of the present invention can have various forms of, for example, medicines, quasi-pharmaceutical products or cosmetics. A case of using them as medicines will be described hereinafter.

In the case where the anti-allergy agent and the mediator release inhibitor of the present invention are used as cosmetics or pharmaceutical cosmetics of quasi-pharmaceutical products, they can be applied to creams, emulsions, lotions, packs and bath agents for sensitive skins or allergy-prone skins. In this case, the anti-allergy agent and the mediator release inhibitor can be appropriately blended with any of an oily or aqueous base, a vitamin agent, a skin softener, a whitening agent, a moisturizer, an antioxidant, a buffer, a UV absorbent, a chelating agent, a pH regulator, a preservative, a thickener, an alcohol material, a cooling agent, a colorant, a fragrance, and the like as needed.

Medicine Containing Anti-Allergy Agent and Mediator Release Inhibitor

The anti-allergy agent and the mediator release inhibitor of the present invention can have various formulations such as medicines depending on use. The formulations in the case include, for example, liquids, ointments, eye-drops, suspensions, patches, injections, powders, tablets, granules, dusting powders, capsules and suppositories.

In the case where the anti-allergy agent and the mediator release inhibitor of the present invention are used as medicines, any of oral administration or parenteral administration is employable.

In particular, the compound represented by the formula (1) or an isomer thereof as well as a salt thereof can be an active ingredient for external medicines having an anti-allergy effect. Here, external medicines are medicines excluding internal medicines and injections and includes, for example, external medicines for skins (dermatologic agents), eye-drops, nasal sprays, and inhalants.

For the anti-allergy agent and the mediator release inhibitor of the present invention, an active ingredient of a compound represented by the formula (1) or an isomer thereof, or a salt thereof can be formulated into a pharmaceutical preparation according to a known pharmaceutical formulation preparation method (see the Japanese Pharmacopoeia, 16th revised version (Public Notice of the Ministry of Health, Labor and Welfare No. 65 of Mar. 24, 2011)).

In this case, the anti-allergy agent and the mediator release inhibitor can be blended with a pharmaceutically-acceptable base, any other pharmaceutically-effective component and an additive, in addition to the active ingredient therein.

The base may be any of an oily base, an emulsion-type base or an aqueous base.

Examples of the other pharmaceutically-effective component include an antiphlogistic analgesic agent, a sterilizing disinfectant, a vitamin agent, a skin softener, a whitening agent and a moisturizer, which can be appropriately used, as needed.

As the additive, for example, any of a buffer, an isotonic agent, a UV absorbent, a chelating agent, a pH regulator, a preservative, a vehicle, a thickener, an alcohol material, a cooling agent, a colorant and a fragrance can be blended.

In the case where the anti-allergy agent and the mediator release inhibitor of the present invention are used as external medicines, the content of the AA derivative may be, for example, 0.0005 to 25 w/v %. The dose frequency is not specifically limited, but can be, for example, once to 6 times/day.

EXAMPLES

The features of the present invention are described more specifically with reference to Examples and Comparative Examples given hereinunder. In the following Examples, the material used, its amount and ratio, the details of the treatment, the treatment process and the like may be suitably modified or changed not overstepping the spirit of the invention. Accordingly, the scope of present invention should not be limitatively interpreted by the Examples mentioned below.

(Synthesis Example 1) Synthesis of Compound 1

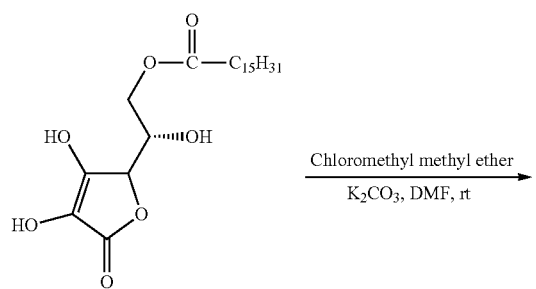

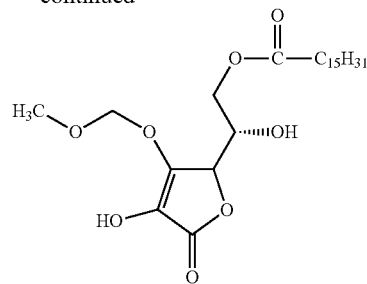

6-O-palmitoyl-L-ascorbic acid (from Tokyo Chemical Industry Co., Ltd.) (3.11 g, 7.5 mmol) was dissolved in N,N-dimethylformamide (60 mL), and potassium carbonate (1.04 g, 7.5×1.0 mmol) and chloromethyl methyl ether (0.56 mL, 7.5 mmol) were added thereto, and reacted at room temperature for 30 minutes. The reaction liquid was separated in ethyl acetate and an aqueous 2 M sodium chloride solution. The ethyl acetate layer was washed with an aqueous 2 M sodium chloride solution, dewatered with sodium sulfate, and concentrated to give 3-O-methoxymethyl-6-O-palmitoyl-L-ascorbic acid at an actual yield of 3.16 g (6.91 mmol).

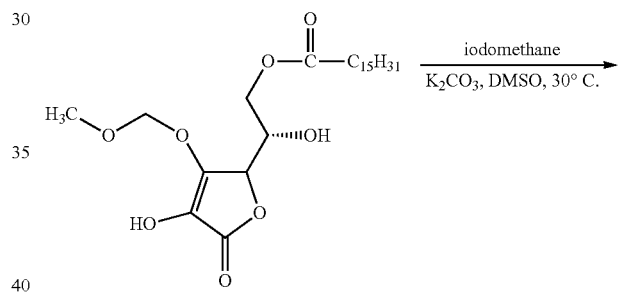

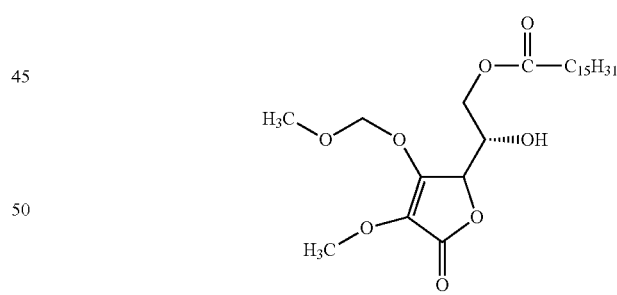

3-O-methoxymethyl-6-O-palmitoyl-L-ascorbic acid (3.16 g, 6.91 mmol) was dissolved in dimethyl sulfoxide (60 mL), and potassium carbonate (1.15 g, 6.91×1.2 mmol) and iodomethane (0.52 mL, 6.91×1.2 mmol) were added thereto, and reacted at room temperature for 45 minutes. The reaction liquid was separated in ethyl acetate and an aqueous 2 M sodium chloride solution. The ethyl acetate layer was washed with an aqueous 2 M sodium chloride solution, dewatered with sodium sulfate, and concentrated to give 2-O-methyl-3-O-methoxymethyl-6-O-palmitoyl-L-ascorbic acid at an actual yield of 2.98 g (6.32 mmol).

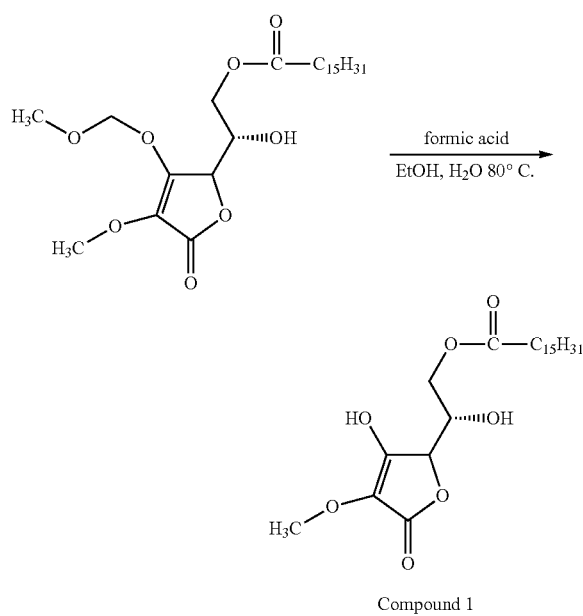

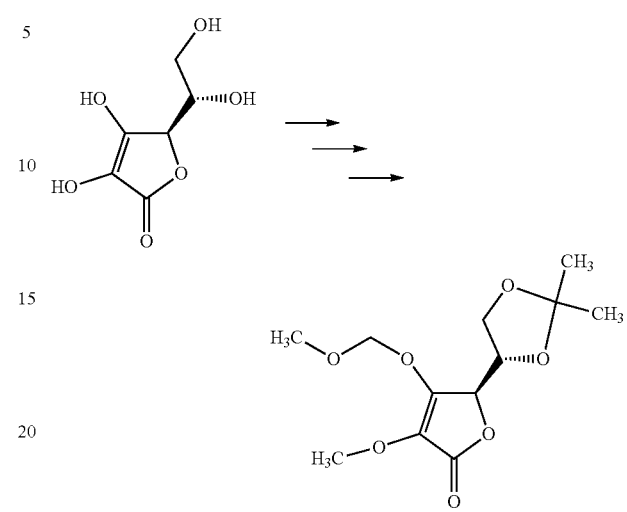

Compound 1

2-O-methyl-3-O-methoxymethyl-6-O-palmitoyl-L-ascorbic acid (2.98 g, 6.32 mmol) was dissolved in a mixed solution (100 mL) of formic acid/ethanol/water=60%/30%/10%, and reacted at 80° C. for 30 minutes. The reaction liquid was concentrated and separated in ethyl acetate and an aqueous 2 M sodium chloride solution. The ethyl acetate layer was washed with an aqueous 2 M sodium chloride solution, dewatered with sodium sulfate, and then concentrated. The resultant concentrate was dissolved in methanol, then adsorbed by cellulose powder, and fed to a silica gel column (Wakogel C-200 (registered trademark) from Wako Pure Chemical Industry Co., Ltd.) to elute the component using an eluent of a mixed solution of 0.5% formic acid-containing toluene/acetone=80%/20%. The eluted fraction was recrystallized from a mixed solvent of n-hexane and ethanol to give the intended compound 1 at an actual yield of 1.41 g (3.29 mmol) and a percent yield of 43.9%. The results of structural analysis of the recrystallized component in NMR and HRMS (high-resolution MS) are shown in Table 1.

TABLE 1

| Carbon Number | $^1$H NMR (600 MHz, CD$_3$OD) δH (ppm) | $^{13}$C NMR (150 MHz, CD$_3$OD) δC (ppm) |
| --- | --- | --- |
| 1 | — | 173.65 |
| 2 | — | 121.90 |
| 3 | — | 159.05 |
| 4 | 4.76 (1H, d, J = 1.8 Hz) | 75.66 |
| 5 | 4.09 (1H, ddd, J = 1.8, 6.6, 7.2 Hz) | 66.41 |
| 6 | 4.16 (1H, dd, J = 6.6, 11.4 Hz) | 64.19 |
|   | 4.24 (1H, dd, J = 7.2, 11.4 Hz) |   |
| 1' | — | 170.97 |
| 2' | 2.36 (2H, t, J = 7.2 Hz) | 33.43 |
| 3' | 1.61 (2H, brqui, J = 7.2 Hz) | 24.54 |
| 4'-15' | 1.27 (24H, m) | 22.30, 28.75, 28.97, 29.04, 29.17, 29.28, 29.33 (x3), 29.36 (x2), 31.65 |
| 16' | 0.88 (3H, t, J = 7.2 Hz) | 13.01 |
| 1" | 3.75 (3H, s) | 58.77 |

ESI-HRMS m/z [M − H]$^-$
C$_{23}$H$_{39}$O$_7$ Theoretical: 427.2701
Measured: 427.2692

(Synthesis Example 2) Synthesis of Compound 2

In acetone (1.0 L), L-ascorbic acid (Wako Pure Chemical Industry Co., Ltd.) (100.00 g, 568 mmol) was reacted with acetyl chloride (8.5 mL, 568×0.21 mmol) added thereto, at room temperature for 18 hours. The reaction liquid was filtered under reduced pressure to collect crude crystals of 5,6-O-isopropylidene-L-ascorbic acid at a yield of 78.17 g (362 mmol).

This 5,6-O-isopropylidene-L-ascorbic acid (78.17 g, 362 mmol) was dissolved in a mixed solvent (280 mL) of tetrahydrofuran/dimethylformamide=75%/25%, potassium carbonate (49.97 g, 362 mmol) and chloromethyl methyl ether (27.2 mL, 362 mmol) were added thereto and reacted at room temperature for 4 hours. Water (250 mL) was added to the reaction liquid to stop the reaction, then neutralized with 2 N hydrochloric acid, and separated with ethyl acetate (250 mL). The ethyl acetate layer was washed with saturated saline water, dewatered with sodium sulfate, and concentrated to give 5,6-O-isopropylidene-3-O-methoxymethyl-L-ascorbic acid at a yield of 32.70 g (127 mmol).

This 5,6-O-isopropylidene-3-O-methoxymethyl-L-ascorbic acid (32.70 g, 127 mmol) was dissolved in a mixed solvent (216 mL) of tetrahydrofuran/dimethyl sulfoxide=50%/50%, potassium carbonate (19.1 g, 139.7 mmol) and iodomethane (8.6 mL, 139.7 mmol) were added thereto and reacted at 30° C. for 3.5 hours. Water (300 mL) was added to the reaction liquid, then neutralized with 2 N hydrochloric acid, and separated with ethyl acetate (300 mL). The ethyl acetate layer was dewatered with sodium sulfate, and concentrated to give 5,6-O-isopropylidene-2-O-methyl-3-O-methoxymethyl-L-ascorbic acid at a yield of 22.17 g.

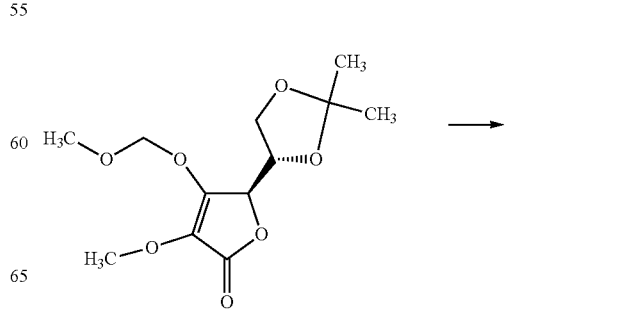

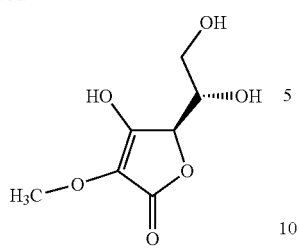

5,6-O-isopropylidene-2-O-methyl-3-O-methoxymethyl-L-ascorbic acid (22.17 g) was dissolved in a mixed liquid (110 mL) of 2 N hydrochloric acid/ethanol=25%/75%, and reacted at 80° C. for 1 hour. The reaction liquid was concentrated, and the resultant concentrate was purified through an aromatic adsorption column (Diaion HP20 from Mitsubishi Chemical Corporation) using an aqueous 0.5% formic acid solution as an eluent to give 2-O-methyl-L-ascorbic acid at a yield of 14.64 g (76.99 mmol).

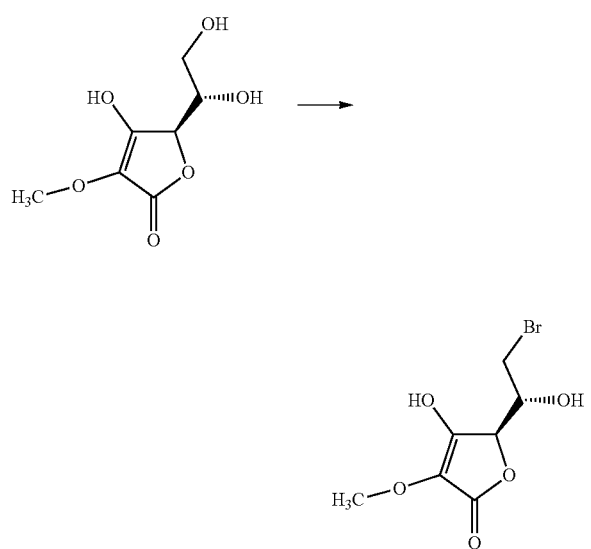

2-O-methyl-L-ascorbic acid (14.64 g, 76.99 mmol) was dissolved in acetic acid (19.1 mL), then an acetic acid solution containing 30% hydrogen bromide (29.7 mL, 153.98 mmol as hydrogen bromide) was added thereto and reacted at 30° C. for 16 hours. The reaction liquid was concentrated, and the resultant concentrate was dissolved in a mixed liquid (75 mL) of 2 N hydrochloric acid/ethanol=50%/50%, and reacted at 60° C. for 3 hours. The reaction liquid was concentrated and the resultant concentrate was separated using ethyl acetate (200 mL) and water (100 mL). The ethyl acetate layer was dewatered with sodium sulfate, and then concentrated. The resultant concentrate was purified through a silica gel column (Wakogel C-200 (registered trademark) from Wako Pure Chemical Industry Co., Ltd.) using a mixed liquid of 0.5% formic acid-containing toluene/acetone=80%/20% as an eluent to give 6-bromo-6-deoxy-2-O-methyl-L-ascorbic acid at a yield of 9.31 g.

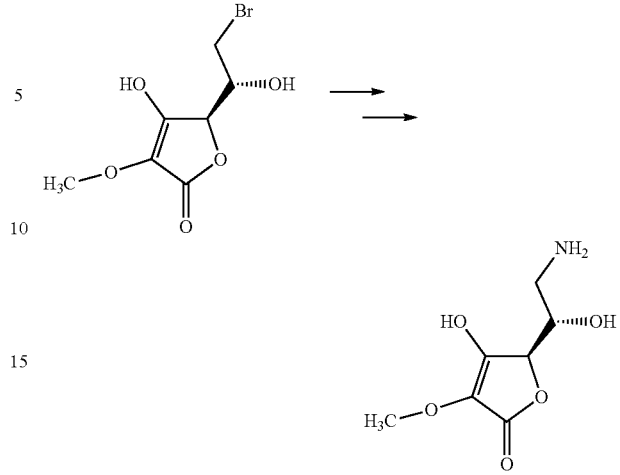

An aqueous solution (160 mL) of sodium azide (3.59 g, 55.2 mmol) and sodium carbonate (7.79 g, 55.2 mmol) was added to 6-bromo-6-deoxy-2-O-methyl-L-ascorbic acid (9.31 g), and reacted at room temperature for 15 hours. The reaction liquid was adjusted to be acidic (pH: about 4.0) with hydrochloric acid, and fed to an aromatic adsorption column (Diaion HP20, from Mitsubishi Chemical Corporation), then an aqueous 0.5% formic acid solution, and 0.5% formic acid-containing 20% methanol, 40% methanol and 60% methanol were made to flow through the column in that order to elute and purify the component to give 6-azide-6-deoxy-2-O-methyl-L-ascorbic acid at a yield of 6.00 g (27.9 mmol).

This 6-azide-6-deoxy-2-O-methyl-L-ascorbic acid (6.00 g, 27.9 mmol) was dissolved in water (100 mL), and hydrogen-reduced at room temperature for 5 hours using palladium carbon (0.36 g, 0.6% by weight) as a catalyst. The reaction liquid was filtered under reduced pressure to remove palladium carbon and then concentrated. The resultant concentrate was adjusted to be acidic (pH: about 4.0) using formic acid, and fed to an active carbon column to elute the component using an aqueous 0.5% formic acid solution as an eluent. The eluted fraction was recrystallized with water to give 6-amino-6-deoxy-2-O-methyl-L-ascorbic acid at a yield of 3.25 g (17.2 mmol).

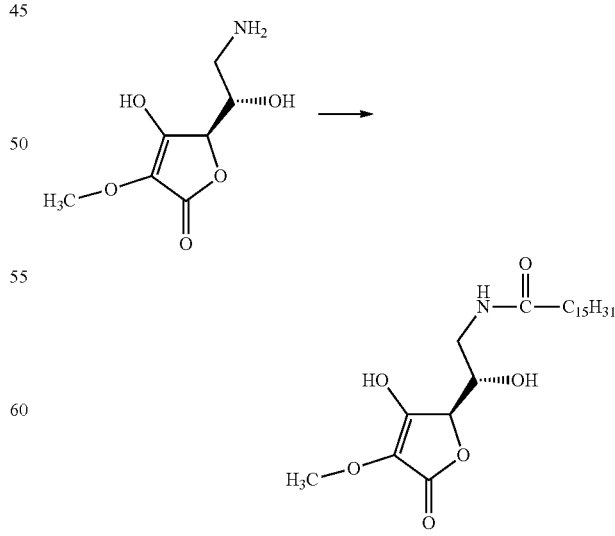

Compound 2

6-Amino-6-deoxy-2-O-methyl-L-ascorbic acid (1.00 g, 5.55 mmol) was dissolved in pyridine (20 mL), and palmitic acid chloride (3.2 mL, 11.1 mmol) was added thereto and reacted at room temperature for 1.5 hours. Methanol (20 mL) was added to the reaction liquid and then concentrated, and the resultant concentrate was separated using methanol and n-hexane. The methanol layer was concentrated and dissolved in ethanol, then adsorbed by a cellulose powder, fed to a silica gel column (Wakogel C-200 (registered trademark), from Wako Pure Chemical Industry Co., Ltd.), and the component was eluted using a mixed liquid of 0.5% formic acid-containing toluene/methanol=80%/20% as an eluent. The eluted fraction was recrystallized with ethanol to give the intended compound 2 at an actual yield of 1.08 g (2.53 mmol) and at a percent yield of 49.2%. The results of structural analysis of the recrystallized component in NMR and HRMS (high-resolution MS) are shown in Table 2.

TABLE 2

| Carbon Number | $^1$H NMR (600 MHz, CD$_3$OD) δH (ppm) | $^{13}$C NMR (150 MHz, CD$_3$OD) δC (ppm) |
|---|---|---|
| 1 | — | 175.52 |
| 2 | — | 121.80 |
| 3 | — | 159.42 |
| 4 | 4.69 (1H, d, J = 1.8 Hz) | 76.22 |
| 5 | 3.98 (1H, ddd, J = 1.8, 6.0, 7.2 Hz) | 67.21 |
| 6 | 3.38 (1H, dd, J = 7.2, 13.2 Hz) 3.43 (1H, dd, J = 6.0, 13.2 Hz) | 41.87 |
| 1' | — | 171.14 |
| 2' | 2.22 (2H, t, J = 7.2 Hz) | 35.57 |
| 3' | 1.61 (2H, brqui, J = 6.6 Hz) | 25.53 |
| 4'-15' | 1.28 (24H, m) | 22.33, 28.90, 29.04, 29.06, 29.22, 29.38 (x6), 31.66 |
| 16' | 0.90 (3H, t, J = 7.2 Hz) | 13.01 |
| 1" | 3.76 (3H, s) | 58.73 |

ESI-HRMS m/z [M − H]$^-$
C$_{23}$H$_{40}$NO$_6$ Theoretical: 426.2861
Measured: 426.2866

Comparative Compounds

Comparative compounds used in Examples are shown below. The left-hand compound (6-sPalm-AA-2G) is an acylated derivative of L-ascorbic acid with an α-D-glucopyranosyl group introduced into the 2-position, and was synthesized according to the method described in PTL 1. The right-hand oxatomide is a commercially-available anti-allergy drug (Wako Pure Chemical Industry Co., Ltd.).

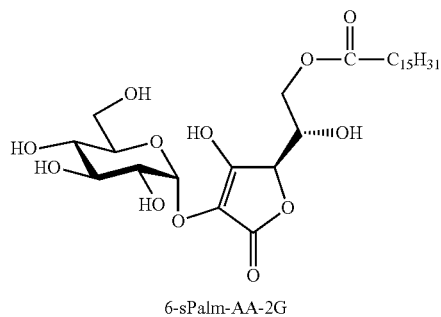

6-sPalm-AA-2G

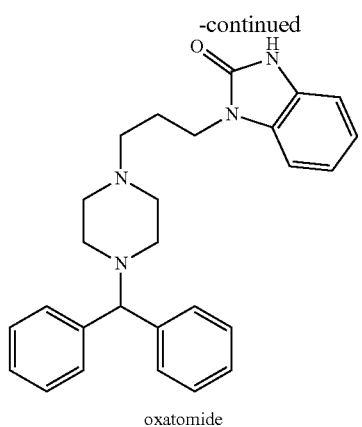

oxatomide

[Example 1] Evaluation of Degranulation Inhibiting Effect

In this Example, the compound 1 and the compound 2 were evaluated in terms of the effect thereof to inhibit degranulation to be induced by stimulation of an antigen-antibody reaction. Degranulation was quantified based on, as an index, β-hexosaminidase release from rat basophilic leukemia cells RBL-2H3. Specifically, β-hexosaminidase is an enzyme released through degranulation of mast cells or basocytes, and through enzymatic reaction with a substrate, p-nitrophenyl-2-acetamide-2-deoxy-β-glucopyranoside, this increases the absorbance at 405 nm of the reaction liquid. Here, the degranulation inhibiting effect was evaluated from the absorbance change as an index of β-hexosaminidase release amount (degree of degranulation).

Reagents, evaluation samples and comparative samples used in this Example were prepared as follows.

Preparation of Reagents (1) MT Buffer (Modified Tyrode Buffer)

Substances of 137 mM sodium chloride, 2.7 mM potassium chloride, 1.8 mM calcium chloride, 1.0 mM magnesium chloride, 5.6 mM (+)-glucose, 20 mM HEPES (4-(2-hydroxyethyl)-1-piperazineethanesulfonic acid), and 0.1% bovine serum albumin (BSA) were dissolved in water to prepare a composition, and adjusted to have a pH of 7.3 with sodium hydroxide.

(2) Anti-DNP-IgE Antibody Solution

An anti-DNP-IgE antibody (the mouse monoclonal anti-DNP IgE antibody, from Sigma Aldrich Corporation) was dissolved in PBS(−) (phosphate buffer physiological saline water not containing Ca and Mg) at 250 mg/mL, and diluted with a 10% FBS-containing DMEM (10% fetal bovine serum-containing Dulbecco's modified Eagle medium) to be a solution thereof at 50 ng/mL.

(3) DNP-HSA Antigen Solution

A human serum albumin labeled with 2,4-dinitrophenyl group (DNP-HSA) (Sigma Aldrich Corporation) was dissolved in PGS(−) at 10 mg/mL, and diluted with an MT buffer to prepare a solution thereof at 500 ng/mL.

(4) Triton Solution

Triton X-100 (Sigma Aldrich Corporation) was diluted with an MT buffer to prepare a 0.1% solution thereof.

(5) P-nitrophenyl-2-acetamide-2-deoxy-β-D-glucopyranoside Solution (Substrate Solution)

Using an aqueous solution of citric acid monohydrate and trisodium citrate dihydrate, a 0.1 M citrate buffer (pH 4.5)

was prepared. P-nitrophenyl-2-acetamide-2-deoxy-β-D-glucopyranoside was dissolved in the 0.1 M citrate buffer at a concentration of 3.3 mM to prepare a solution thereof.

(6) Glycine Solution (Enzymatic Reaction Stop Solution)

Glycine was dissolved in water at a concentration of 2 M, and adjusted to have a pH of 10.4 with sodium hydroxide.

Preparation of Evaluation Samples and Comparative Samples

The compound 1 and the compound 2 were individually dissolved in a 0.25% dimethyl sulfoxide-containing MT buffer at a concentration of 40 μM, 60 μM or 80 μM to prepare solutions to be evaluation samples. On the other hand, as comparative samples, 6-sPalm-AA-2G was dissolved in a 0.25% dimethyl sulfoxide-containing MT buffer at a concentration of 40 μM, 60 μM or 80 μM to prepare solutions, and oxatomide was dissolved in a 0.25% dimethyl sulfoxide-containing MT buffer at a concentration of 75 μM to prepare a solution.

Test Cells

In this Example, rat basophilic leukemia cells RBL-2H3 bought from a human science cell bank (JCRB) were suspended in a 10% FBS (decomplemented)-containing DEME, and incubated in the presence of 5% $CO_2$ at 37° C., and these were used in the test.

Degranulation Inhibiting Test

First, RBL-2H3 cells incubated in a 10% FBS-containing DMEM were peeled in a trypsin solution, sowed in a 96-well flat bottom multiplate at a density of $5.0 \times 10^4$ cells/200 μL/well, and incubated for 24 hours. The supernatant in each well was removed, then an anti-DNP-IgE antibody solution (50 ng/mL, 100 μL) was injected into each well, and incubated in the presence of 5% $CO_2$ at 37° C. for 2 hours. After the incubation, the cell layer in each well was washed twice with an MT buffer heated at 37° C. to remove the anti-DNP-IgE antibody. Subsequently, each solution of the compound 1 and the compound 2 as an evaluation sample, each solution of 6-sPalm-AA-2G and oxatomide as a comparative sample, and a MT buffer as a control were individually injected to each well in an amount of 90 μL/well, and incubated in the presence of 5% $CO_2$ at 37° C. for 20 minutes. Further, a DNP-HSA antigen solution (500 ng/mL, 10 μL) was injected into each well to attain antigen-antibody reaction therein for 60 minutes, and then cooled with ice for 10 minutes to stop the reaction. A part (20 μL) of the supernatant of each well was dispensed in an empty well, and after the remaining supernatant was removed, a Triton solution (100 μL) was added to the residual cell layer, shaken in a plate shaker at 500 rpm for 5 minutes to disrupt the cells. The disrupted cell liquid (20 μL) was dispensed in each well of a different 96-well flat bottom microplate.

Each supernatant dispensed in the empty well after the antigen-antibody reaction, and the disrupted cell liquid dispensed in each well of the different 96-well flat bottom microplate each were heated at 37° C. for 5 minutes, and then a substrate solution of a p-nitrophenyl-2-acetamide-2-deoxy-β-D-glucopyranoside solution (40 μL) was added thereto to carry out enzymatic reaction at 37° C. for 90 minutes. Subsequently, an enzymatic reaction stop liquid of a glycine solution (40 μL) was injected into each well to stop the enzymatic reaction, and after the stop of the enzymatic reaction, the absorbance (S) at 405 nm of the supernatant and the absorbance (CL) at 405 nm of the disrupted cell liquid were measured. Apart from those that had been made to experience the enzymatic reaction, each supernatant dispensed in an empty well after the antigen-antibody reaction, and the disrupted cell liquid dispensed in each well of a different 96-well flat bottom microplate were individually heated at 37° C. for 5 minutes, then a glycine solution (40 μL) was added thereto, and a p-nitrophenyl-2-acetamide-2-deoxy-β-D-glucopyranoside solution (40 μL) was added, and incubated at 37° C. for 90 minutes. Subsequently, the absorbance (Sc) at 405 nm of each supernatant and the absorbance (CLc) at 405 nm of the disrupted cell liquid were measured.

Using the measured values of absorbance, a release ratio (degranulation ratio) of β-hexosaminidase was calculated according to the following equations (I) and (II) to achieve the release inhibition ratio (degranulation inhibition ratio) of β-hexosaminidase. The results are shown in FIG. 1. In FIG. 1, the data were expressed as an average value±standard deviation. Comparison among multigroup average values was achieved in a Dunnett's test after one-way analysis of variance, and those having a significant level p of less than 0.05 were judged to have a significant difference. In FIG. 1, "**" shows $p<0.01$.

$$\text{Degranulation Ratio (\%)} = [(S-Sc)/\{(S-Sc)+(CL-CLc)\}] \times 100 \quad (I)$$

S: Absorbance of a supernatant added with an enzymatic reaction stop solution after addition of a substrate solution thereto.

Sc: Absorbance of a supernatant added with a substrate solution after addition of an enzymatic reaction stop solution thereto.

CL: Absorbance of a disrupted cell liquid added with an enzymatic reaction stop solution after addition of a substrate solution thereto.

CLc: Absorbance of a disrupted cell liquid added with a substrate solution after addition of an enzymatic reaction stop solution thereto.

$$\text{Degranulation Inhibition Ratio (\%)} = 100 - (\text{degranulation ratio of sample}/\text{degranulation ratio of control}) \times 100 \quad (II)$$

As shown in FIG. 1, the β-hexosaminidase release inhibition ratio (degranulation inhibition ratio) of the system added with any of the compound 1 and the compound 2 is greatly higher than the degranulation inhibition ratio of the system added with 6-sPalm-AA-2G, and surpasses the degranulation inhibition ratio of the system added with oxatomide. From these, it is known that an alkyl group is far more advantageous than a glycosyl group as the group to be introduced into the 2-position of ascorbic acid and that, when an ascorbic acid is converted into a derivative having a structure represented by the formula (1), a compound having a high degranulation inhibiting effect and useful as a mediator release inhibitor can be realized. It is also known that, between the compound 1 and the compound 2, the compound 2 with an acylamino group introduced into the 6-position thereof tends to have a higher degranulation inhibiting effect than the compound 1 with an acyloxy group introduced into the 6-position thereof.

[Example 2] Evaluation of PCA Reaction Inhibiting Effect

In this Example, the anti-allergy activity of the compound 1 and the compound 2 was evaluated based on, as an index, the inhibiting effect thereof against PCA (passive cutaneous anaphylaxis) reaction. PCA reaction is a series of cell reaction of an allergy reaction including immobilization of mast cells via an Fc part of immunoglobulin, antigen-antibody reaction on the cells, release of inflammatory mediator from the mast cells through the reaction and promotion of vascular permeability. Here, after an anti-DNP-IgE antibody solution has been subcutaneously administered to a test body, a solution containing a 2,4-dinitrophenyl group (DNP)-labeled human serum albumin (HSA) and a dye (Evans blue) (DNP-HSA-Evans blue solution) is intravenously administered, and the vascular permeability increase according to the antigen-antibody reaction is quantified by the absorbance increase owing to dye leakage from the blood vessel to the tissue to thereby evaluate the PCA reaction inhibiting effect.

Reagents, evaluation samples and comparative samples used in this Example were prepared as follows.

Preparation of Reagents (1) Aqueous 0.9% Sodium Chloride Solution

Sodium chloride was dissolved in pure water at a concentration of 0.9%, and sterilized by filtration through a 0.22 µm filter to prepare the solution.

(2) Anti-DNP-IgE Antibody Solution

An anti-DNP-IgE antibody was dissolved in DPBS(−) (Dulbecco's phosphate buffer physiological saline water not containing Ca and Mg) at a concentration of 250 µg/ml, and adjusted to have a concentration of 5 µg/mL with an aqueous 0.9% sodium chloride solution.

(3) DNP-HAS-Evans Blue Solution

Evans blue (Sigma Aldrich Corporation) was dissolved in an aqueous 0.9% sodium chloride solution at a concentration of 1% (w/v) to prepare a dye solution, and a 2,4-dinitrophenyl group-labeled human serum albumin (DNP-HAS) was dissolved in the dye solution at a concentration of 0.4 mg/mL.

Preparation of Evaluation Samples and Comparative Samples

The compound 1 and the compound 2 were individually dissolved in a diluting liquid of DPBS(−)/ethanol/glycerol/Tween 20 (Wako Pure Chemical Industry Co., Ltd.)=74.5%/20%/5%/0.5% (v/v) to prepare solutions to be evaluation samples. 6-sPalm-AA-2G and oxatomide were individually dissolved in the above diluting liquid to prepare solutions to be comparative samples.

Test Animal

In this Example, ICR male mice (7-week age) bought from CLEA Japan Inc. were used for the test.

PCA Reaction Inhibition Test

First, under anesthesia, 20 µL of an anti-DNP-IgE antibody solution was subcutaneously administered to the auricle of each of eight ICR male mice (7-week age), and in 24 hours after the subcutaneous administration, under anesthesia, a solution of the compound 1 of an evaluation sample was applied to the auricle. At that time, the amount of the solution of the compound 1 applied was 30 µL (90 nmol as the compound 1)/auricle. In 3.5 hours after the application of the solution, a DNP-HAS-Evans blue solution (0.25 mL) was intravenously administered to the mice. With that, in 30 minutes after the intravenous administration, the mice was killed by cervical dislocation, and the auricle was cut off.

An aqueous 1 N potassium hydroxide solution (0.5 mL) was added to the thus-cut auricle, and shaken at 37° C. overnight. After shaking, a mixed solution (3.25 mL) of aqueous 0.34 M phosphoric acid solution/acetone=13/5 (v/v) was added, and centrifuged by 700×g at 4° C. for 20 minutes, and the absorbance at 620 nm of the supernatant was measured.

In place of the solution of the compound 1, a solution of the compound 2 of an evaluation sample, an oxatomide solution and a 6-sPalm-AA-2G solution of comparative samples, and a diluting liquid as a control were similarly tested according to the PCA reaction inhibition test. The amount of the 6-sPalm-AA-2G solution applied is 150 nmol/auricle.

Figure 2:
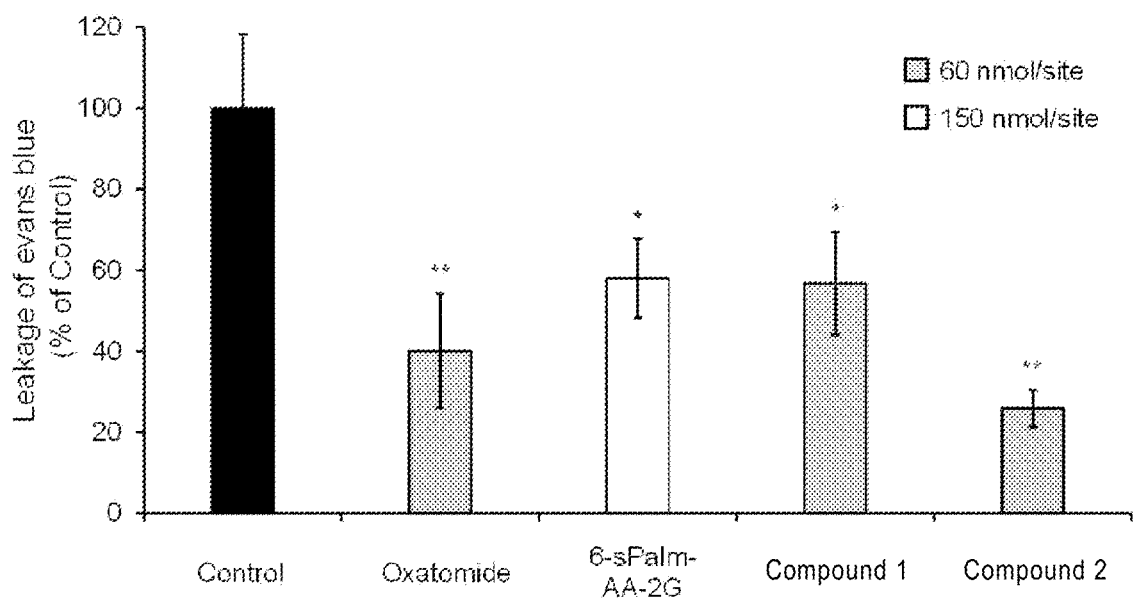
FIG. 2 This is a graph showing a dye leakage amount in PCA reaction in mice given compound 1, compound 2, 6-sPalm-AA-2G or oxatomide.

The absorbance measured in each system was converted into a relative value based on the absorbance in the control, 100, and shown in FIG. 2. The relative value of absorbance corresponds to the leakage of the dye leaked out of the blood vessel. In FIG. 2, the data are expressed as an average value±standard deviation. Comparison among multigroup average values was achieved in a Dunnett's test after one-way analysis of variance, and those having a significant level p of less than 0.05 were judged to have a significant difference. In FIG. 2, "*" shows p<0.05, and "**" shows p<0.01.

As shown in FIG. 2, the dye leakage in the system where the compound 1 or the compound 2 had been applied was lower than the dye leakage in the system with 6-sPalm-AA-2G where the quantity of application was 2.5 times, and especially in the system where the compound 2 had been applied, the dye leakage was suppressed more than that in the system where oxatomide had been applied. These results confirm that, as the group to be introduced into the 2-position of ascorbic acid, an alkyl group is more advantageous than a glycosyl group. In addition, it is confirmed that the compound represented by the formula (1) can express a high anti-allergy activity in vivo. In addition, it is known that, between the compound 1 and the compound 2, the compound 2 with an acylamino group introduced into the 6-position thereof tends to have a higher anti-allergy activity than the compound 1 with an acyloxy group introduced into the 6-position thereof.

INDUSTRIAL APPLICABILITY

By using the compound of the present invention, an anti-allergy agent and a mediator release inhibitor that have a high anti-allergy activity and a high mediator release inhibiting effect and are highly safe can be realized. Consequently, the industrial applicability of the present invention is great.

The invention claimed is:

1. A compound represented by the following formula (1):

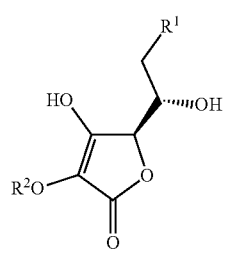

Formula (1)

wherein $R^1$ represents a substituted or unsubstituted acyloxy group having 10 or more carbon atoms, or a substituted or unsubstituted acylamino group having 10 or more carbon atoms, and $R^2$ represents a substituted or unsubstituted alkyl group having 1 to 10 carbon atoms.

2. The compound according to claim 1, wherein $R^1$ in the formula (1) is a substituted or unsubstituted acylamino group having 10 or more carbon atoms.

3. The compound according to claim 1, wherein $R^1$ in the formula (1) is an unsubstituted acyloxy group having 10 or more carbon atoms or an unsubstituted acylamino group having 10 or more carbon atoms.

4. The compound according to claim 1, wherein the alkyl group of $R^2$ in the formula (1) has 1 to 6 carbon atoms.

5. The compound according to claim 1, wherein $R^2$ in the formula (1) is an unsubstituted alkyl group having 1 to 10 carbon atoms.

* * * * *